United States Patent [19]

Colbert

[11] Patent Number: 4,593,401
[45] Date of Patent: Jun. 3, 1986

[54] ENDODONTIC FILM HOLDER

[76] Inventor: James J. Colbert, 5106 W. 47th St., Sioux Falls, S. Dak. 57106

[21] Appl. No.: 594,922

[22] Filed: Mar. 29, 1984

[51] Int. Cl.$^4$ .......................... A61B 6/14; G03B 42/04
[52] U.S. Cl. ..................................................... 378/168
[58] Field of Search ............... 378/167, 168, 169, 170, 378/181

[56] References Cited

U.S. PATENT DOCUMENTS 2,926,256  2/1960  Rankin ................................. 378/167
4,114,044  9/1978  Chiulli ................................. 378/167

Primary Examiner—Carolyn E. Fields
Attorney, Agent, or Firm—B. Craig Killough

[57] ABSTRACT

An endodontic film holder is disclosed which holds radiographic film in place for the taking of X-rays without necessitating removal from the tooth the endodontic file which is used during the root canal procedure. The device incorporates a dental floss loop to facilitate removal of the device and may be used in conjunction with a rubber dam and clamp.

7 Claims, 9 Drawing Figures

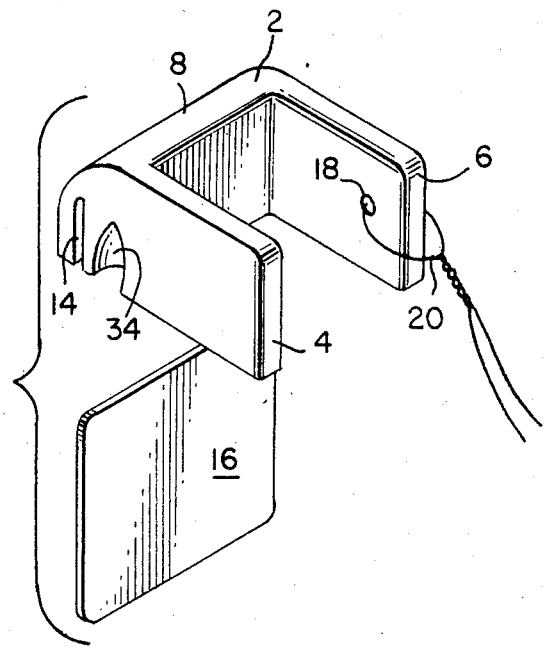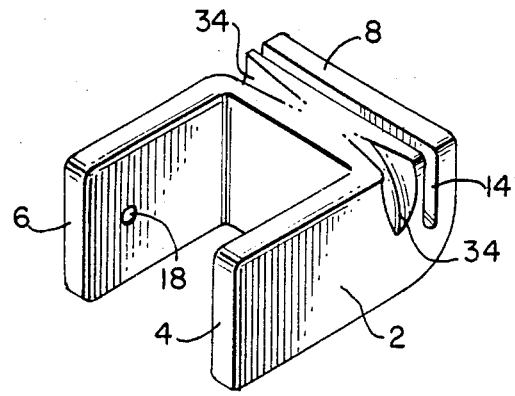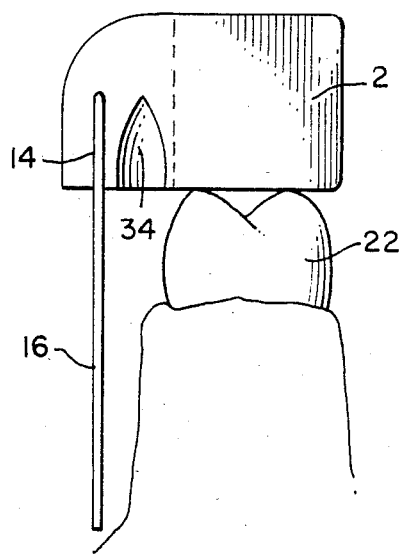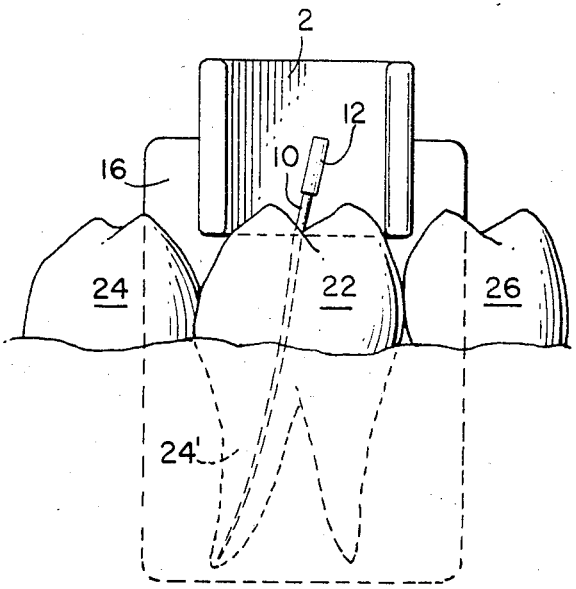

ENDODONTIC FILM HOLDER

BACKGROUND AND SUMMARY OF THE INVENTION

This invention relates generally to radiographic film holders of the type used for dental X-rays, and more particularly to an endodontic film holder which may be used during the endodontic (root canal) procedure.

During the endodontic, or root canal, procedure, an endodontic file is used to remove the nerve from the tooth and cleanse the nerve tract within the root of the tooth. While the file is in place in the tooth, it is necessary to X-ray the tooth to assure that the endodontic file has been inserted deeply enough into the root of the tooth so that all of the nerve tract will be removed. This procedure must be done with the file in place and before it is removed.

The prior art discloses various forms of dental X-ray film holders. However, these devices are generally designed for use in diagnostic X-ray procedures, and none of the devices contemplate being used in conjunction with endodontic files and the root canal procedure. Prior to the present invention, it has been necessary to manually hold the film in place during the endodontic procedure, exposing the patient, the dentist, the dental assistant, or all of them to undue radiation. Many dentists have experienced deformation of their hands and fingers due to prolonged radiation exposure.

Rubber dams are used during dental procedures to keep saliva and foreign materials away from the tooth and area upon which the procedure is being performed. They are commonly and frequently used during the endodontic procedure, being clamped very near the subject tooth. Since the prior art discloses devices which are primarily for use with diagnostic X-ray procedures, the prior art does not provide for the use of a rubber dam while the X-ray is being taken.

Accordingly, it is the primary object and purpose to provide an endodontic film holder which holds and orients radiographic film during the endodontic procedure and while endodontic files are in place within the tooth.

It is an additional object of the invention to eliminate unnecessary radiation exposure to dentists, dental assistants and patients.

It is a further object of the invention to provide a radiographic film holder which may be easily and quickly positioned and removed from the patient's mouth.

Yet another object of the invention is to provide a radiographic film holder which may be used while rubber dams and rubber dam clamps are in place.

DESCRIPTION OF THE DRAWINGS

FIG. 1 is an exploded perspective view of the device and radiographic film, with a dental floss loop in place in the device.

FIG. 2 is a perspective view of the device being essentially inverted from FIG. 1, showing with particularity the slot into which the radiographic film is inserted, and the curved void for reception of the rubber dam clamp.

FIG. 3 is a side elevation showing the device with radiographic film in place and positioned over a posterior tooth.

FIG. 4 is an elevation and partial phantom showing the device in place over a posterior tooth with an endodontic file inserted into the tooth and radiographic film in place.

DETAILED DESCRIPTION OF THE PREFERRED EMBODIMENT

Figure 5:
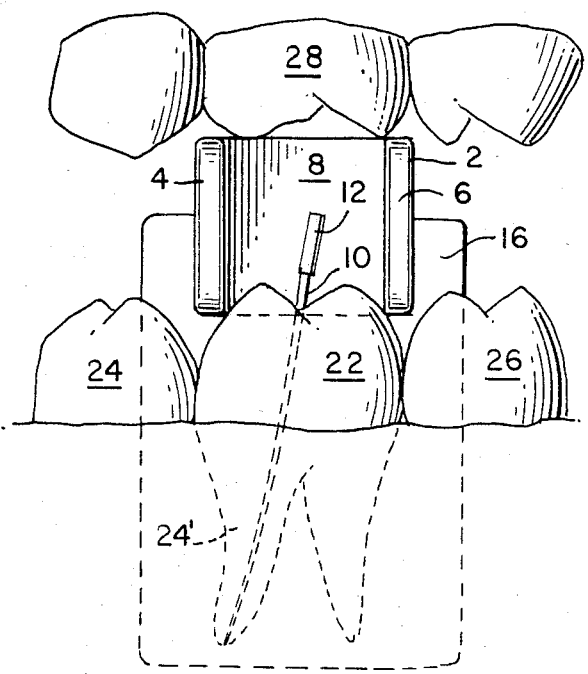
FIG. 5 is a view identical to FIG. 4 except that the upper teeth are closed over the device to hold it in place.

The endodontic, or root canal, procedure is used to remove the nerve from the tooth and clense the nerve tract within the root of the tooth. It is necessary to X-ray the tooth with the endodontic file in place to insure that all of the nerve tract has been removed and that the file has been inserted to the proper depth. The file itself is below the surface of the tooth and into the root, while the handle of the file extends above the surface of the tooth. Radiographic film holders in the prior art do not allow for the presence of the file handle, and cannot be used in the endodontic procedure.

Briefly, and as shown in the drawings, the endodontic film holder is a generally U-shaped or box shaped one piece member 2, having two generally parallel sides 4,6 which are generally perpendicular to a third side 8. By being three sided or U-shaped, the device provides a void for the presence of the endodontic file 10 and file handle 12. The third side 8 is generally thicker than the parallel sides 4,6, having a slot 14 therein for reception of the radiographic film 16, and as will appear, to facilitate the use of a rubber dam. One of the parallel sides 6 has a hole 18 therein through which a loop of dental floss 20 may be inserted and tied to facilitate removal of the device from the mouth.

Radiographic film 16, which is generally a rectangular plane in shape, is inserted into the slot 14 in the U-shaped or box shaped member 2. This assembly is then placed over the tooth 22 on which the procedure is being performed, as shown in FIGS. 3, 4 and 5, properly positioning the radiographic film 16 so that the entire root 24 and nerve tract of the tooth is X-rayed. By being U-shaped or box shaped, the holder member 2 leaves a void which surrounds but does not interfere with the positioning of the endodontic file 10. The member 2 is held in place by resting upon the tooth 22 on which the procedure is being performed, as well as support from surrounding teeth, the radiographic film 16, and the clamping force of the upper 28 and lower sets of teeth 22,24,26 against the holder member 2. After the X-ray is taken, the assembly may be quickly and easily removed by manually grasping the dental floss loop 20 inserted through the hole 18, and taking the member 2 with film 16 in place from the patient's mouth.

The invention in the preferred embodiment may also be used in conjunction with a rubber dam 28 and rubber dam clamp 30. A rubber dam is a device which is used to isolate a tooth upon which a dental procedure is being performed to prevent saliva build-up and to keep dental instruments, such as endodontic files, from being inhaled, swallowed or from falling into the patient's throat. The rubber dam is essentially a sheet of rubber contained in a frame, and has a void or hole therein through which the subject tooth may be isolated. The rubber dam clamp then holds the rubber dam in place, clamping the rubber dam in place near the tooth and isolating the tooth. Rubber dams are commonly and frequently used in the endodontic procedure.

Figure 6:
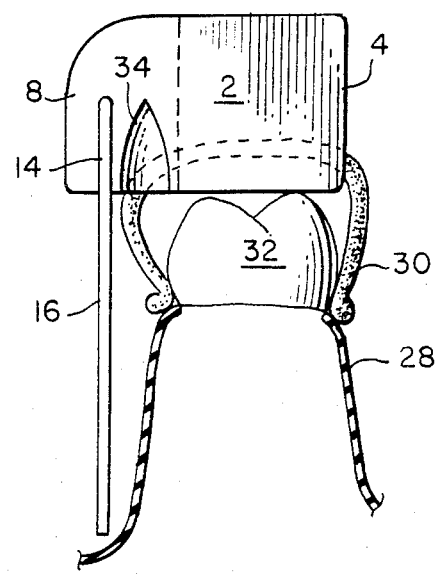
FIG. 6 is a side sectioned, elevation showing the device positioned over a posterior tooth, with radiographic film in place, and being used in conjunction with a rubber dam and a posterior rubber dam clamp.
Figure 7:
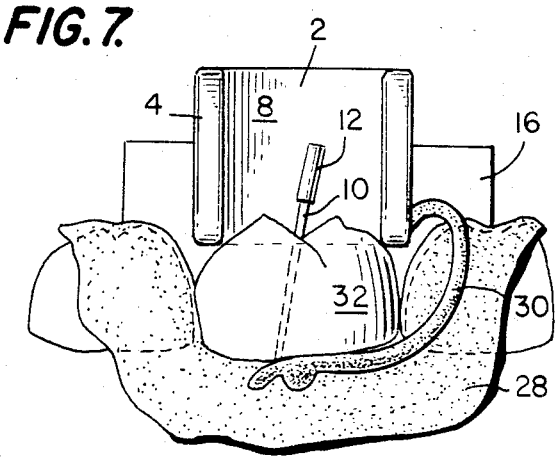
FIG. 7 is an isolation showing the device in place and as used with a rubber dam and posterior rubber dam clamp, with an endodontic file shown as a partial phantom.

To use the device with a rubber dam 28, the holder member 2 is positioned with the film 16 attached making sure that the rubber dam 28 is between the tooth 32 and the film 16, as shown in FIGS. 6 and 7. The member 2 may be inserted over the rubber dam clamp 30, fitting within a generaly curved depression or void 34 in the holder member. The depression or void 34 is molded into the one piece member 2 in the third side 8, being located between the slot 12 for the location of the radiographic film 16 and the tooth 32 when the device is in position. The endodontic file 10 is in position in the tooth 32 just as when the device is used without the rubber dam.

Figure 8:
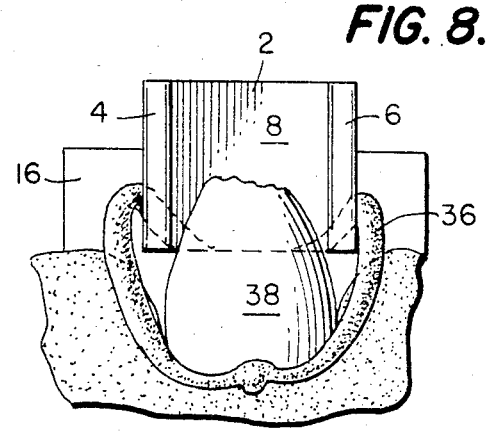
FIG. 8 is an isolation showing the device in place over an anterior tooth, using a rubber dam and anterior rubber dam clamp and showing the rubber dam clamp as a partial phantom.
Figure 9:
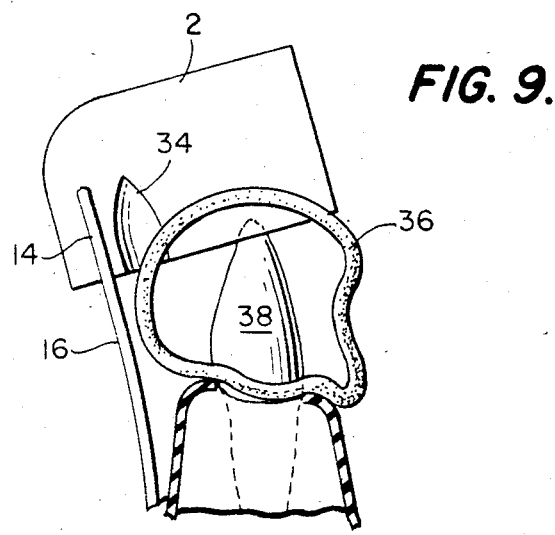
FIG. 9 is a sectioned, elevation showing the device in position over an anterior tooth, with radiographic film in place and used in conjunction with an anterior rubber dam clamp.

The device may also be used with anterior rubber dam clamp 36, which is of the type as shown in FIG. 8 and 9. The member 2 fits over the tooth 38 and over the rubber dam clamp 36, with the rubber dam clamp 36 running in the void 34 on each side of the device.

The film holder may be made of any suitable material such as various plastics, or rubber. The chosen material should be able to be sterilized and radiolucent so as not to interfere with the X-ray process.

What is claimed is:

1. A radiographic film holder, comprising a one-piece, three-sided, box-shaped member means for placement over a tooth and for resting on said tooth so as to surround an endodontic file which is present in said tooth, and further having a slot therein into which radiographic film is inserted parallel to the direction of growth of said tooth.

2. A radiographic film holder as described in claim 1, wherein said one-piece, box-shaped member means includes removal means, said removal means comprising a hole in one side thereof for receiving a loop of dental floss.

3. A radiographic film holder as described in claim 2, wherein said one-piece, box-shaped member means has a curved void means therein to facilitate reception of a rubber dam clamp.

4. A radiographic film holder as described in claim 1, wherein said one-piece, box-shaped member means has a curved void means therein to facilitate reception of a rubber dam clamp.

5. A radiographic film holder, comprising a one-piece, generally U-shaped member having a slot therein which is perpendicular to the plane of said "U" and into which radiographic film is inserted, and further having a curved void means therein to facilitate reception of a rubber dam clamp.

6. A radiographic film holder comprising:
   a. a one-piece, generally U-shaped member having a slot therein which is perpendicular to the plane of said "U" and into which radiographic film is inserted, and further having a hole through one point of said "U"; and
   b. means for facilitating removal of said member, said means comprising a loop of dental floss which is inserted through said hole.

7. A radiographic film holder as described in claim 6, wherein said one-piece, box-shaped member has a curved void means therein so as to facilitate reception of a rubber dam clamp.

* * * * *